United States Patent [19]

Landsberger

[11] Patent Number: 4,738,955
[45] Date of Patent: Apr. 19, 1988

[54] ANTI-CARCINOMA THERAPEUTIC AGENT OF GLYCOSAMINOGLYCANS AND CYTOSTATIC AGENTS

[76] Inventor: Albert Landsberger, Lerchenweg 6, D-6901 NuBloch, Fed. Rep. of Germany

[21] Appl. No.: 770,505

[22] Filed: Aug. 28, 1985

[30] Foreign Application Priority Data

Sep. 5, 1984 [DE] Fed. Rep. of Germany ....... 3432661

[51] Int. Cl.$^4$ .......................................... A61K 31/725
[52] U.S. Cl. ..................................... 514/56; 424/94.1; 424/94.6
[58] Field of Search ............................. 424/94; 514/56

[56] References Cited

U.S. PATENT DOCUMENTS

| 4,029,767 | 6/1977 | Vairel et al. | 514/56 |
| 4,389,392 | 6/1983 | Adachi | 530/395 |
| 4,565,806 | 1/1986 | Setala | 514/56 |

FOREIGN PATENT DOCUMENTS

| 0114589 | 8/1984 | European Pat. Off. | 514/56 |
| 3220326 | 12/1983 | Fed. Rep. of Germany | |
| 2062468 | 5/1981 | United Kingdom | 514/56 |
| 2131691 | 6/1984 | United Kingdom | 514/56 |

OTHER PUBLICATIONS

Ishida et al., *JBC*, 258(a), 1983, pp. 5933–5937.
Lipinski et al., *J. Immunol.*, 1982, p. 2301.
Wiels et al., *Cancer Res.*, 1984, p. 129.
Nirdelmon et al., Science, 220, 1983, p. 509.
Journal of Medicinal Chemistry, 1974, vol. 17, No. 12, p. 1335.
Hoppe-Seyler's Z. Physiol. Chem., 357, S., 499–508, Apr. 1976.

*Primary Examiner*—John Kight
*Assistant Examiner*—Garnette D. Draper
*Attorney, Agent, or Firm*—Scully, Scott, Murphy & Presser

[57] ABSTRACT

A combination consisting of a mixture comprising high-molecular and low-molecular glycosaminoglycan polysulfates as well as a cytostatic agent is effective to obtain improved results in selectively killing quiescent tumor cells. This effect may be reinforced by adding a lipolytic and/or proteolytic enzyme.

13 Claims, No Drawings

ANTI-CARCINOMA THERAPEUTIC AGENT OF GLYCOSAMINOGLYCANS AND CYTOSTATIC AGENTS

The invention relates to a therapeutic preparation containing glycosaminoglycan polysulfates and at least one cytostatic agent in addition to other carrier and accompanying substances.

In substance, conventional methods used to treat malignant tumors are limited to surgical and/or radiological treatments, and to the application of cytostatic agents. The disadvantages inherent in radiological and cytostatic methods of treatment are well known. Currently used clinical treatments, mostly based on several cytostatic agents, destroy tumor cells almost exclusively while they are in the cell division stage. During the so-called quiescent phase, cancer cells are hardly ever attacked by cytostatic drugs. With most types of cancer, however, cells are preponderantly quiescent. Accordingly, good clinical results due to cytostatic chemotherapy in its usual clinical form have been reported only for those tumors characterized by a high ratio of cell division, such as Hodgkin's and non-Hodgkin lymphomas, as well as certain types of leukemia. Moreover, cytostatic chemotherapy is further limited by its substantial side effects, mostly due to the fact that cytostatic agents attack even normal tissue cells.

From the "Journal of Medicinal Chemistry, 1974, Vol. 17, No. 12, p. 1335", it is known that the efficacy of treating tumors with cytostatic agents may be increased by simultaneously administering heparin. According to observations, patients non-responsive to treatments with cytostatic agents devoid of heparin responded better if heparin was used as an accompanying substance. Even heparin, however, does not provide a substance permitting significant improvements in the efficacy of cytostatic agents. Moreover, heparin failed to protect healthy tissue cells against cytostatic drugs, i.e. to decrease side effects. On the contrary, additional internal bleeding occurred when this therapy was applied, which bleeding made it more difficult to administer heparin together with cytostatic agents.

From DE-OS No. 32 20 326, it is known that cytostatic treatment of tumors may be improved significantly by administering glycosaminoglycan polysulfates other than heparin. This therapeutic preparation is capable of selectively "opening" tumor cells and of introducing cytotoxically or cytolytically effective substances in a well-targeted manner. Thus, healthy tissue cells remain largely or wholly unaffected by cytostatic drugs, which are administered at substantially lower dosage levels so that serious side effects otherwise entailed by conventional clinical applications of cytostatic chemotherapy are substantially reduced, or obviated at all.

Even this anti-carcinoma therapy has been found not to attack a certain fraction of tumor cells while they are in their quiescent phase.

Thus, it is the object of this invention to provide a therapeutic preparation of enhanced efficacy, above all as regards quiescent tumor cells, and therefore of generally increased selectivity. Said preparation is intended to attack and destroy tumor cells in a more specific and permanent manner, i.e. both when said cells dividing and while they are quiescent.

Based on a therapeutic preparation in accordance with the generic part of the principal claim, this object is attained by the features indicated in the characterizing part of said claim.

Glycosaminoglycan polysulfates, also designated sulfated polyanions, and formerly called mucopolysaccharide polysulfuric acid esters, are agents known to be used in the treatment of various diseases. Among other substances, this class of compounds includes heparins, the physiologically coagulation-inducing effects of which have long been exploited. Other compounds belonging to this class of substances (e.g. heparins and heparinoids) are used to treat hyperlipemias and hypercholesteremias, or as antiarthrotic agents (e.g. extracts of cartilage and chondroitin polysulfate). Moreover, the substances under review were known to have pronounced and specific inhibitory effects on enzyme systems (Shaffrath et al., in: Hoppe-Seylers Z. Physiol. Chem. 357, 499 (1976)). Now, however, studies on biocytocultures found that, as compared to benign cells, malignant cells preferentially absorb and store the glycosaminglycan polysulfates according to the invention.

Increased absorption of glycosaminoglycan polysulfates inhibits biosynthetic performances within the cellular metabolism of malignant cells. Thus, there is synergism as regards the effects of simultaneously used cytostatic agents which, therefore, can be administered in concentrations that are not, or only slightly, detrimental to benign cells.

Cytostatic agents to be used according to the invention include, but are not limited to, alkylating cytostatic agents such as nitrogenous mustard-gas and ethylene imine derivatives; antimetabolites such as methotrexate; antagonists of purine and pyrimidine bases cytostatically effective antibiotics; and alkaloids such as cholchicine or vincristin.

Furthermore, it has been found very advantageous indeed to add at least one proteolytic and/or lipolytic enzyme such as trypsin to said therapeutic preparation. The effect so produced was found to be extraordinarily surprising. After all, according to the consensus of biochemical experts, a proteolytic enzyme such as trypsin will interact with glycosaminoglycan polysulfates so as to neutralize the effectiveness of both substances. Due to said body of knowledge, no person versed in the art could have been expected to keep working towards this invention. As shown by the experimental results set forth in this patent application there is, due to interactions not yet fully understood between all the substances used according to this invention, not an inhibitive but, in an utterly unexpected manner, a synergistic effect.

The biochemical literature describes trypsin as a cytolytic substance that will selectively attack any malignant cell already damaged by additional administration of the mixture of glycosaminoglycan polysulfates according to the invention. Adding at least one type of proteolytic and/or lipolytic enzyme, such as trypsin, is of importance because there will be biologically resistant species within any individual strain of tumor cells. Said resistant tumor cells are predigested by the one or several enzymes used so as to permit the cytostatic agent used to be efficacious. Said one or several enzymes used enhance, as regards malignant cells, the selective efficacy of the preparation according to the invention and thus permit the highly specific use of one of several cytostatic agents at low dosage levels which would, if administered at therapeutically effective, i.e. much more massive, dosage levels, damage all cells, even benign ones. Glycosaminoglycan polysulfate mixtures, possibly used together with at least one proteolytic and/or lipolytic enzyme such as trypsin, will selectively "open" tumor cells permitting specifically effective cytotoxic or cytolytic substances to be introduced; in this context, any enzyme so used will likewise be cytolytically effective.

Studies performed have demonstrated that a therapeutic preparation containing at least two glycosaminoglycan polysulfates characterized by differing molecular weights and at least one cytostatic agent as well as, if present, at least one proteolytic and/or lipolytic enzyme such as trypsin is significantly more effective in attacking and destroying tumor cells as the therapeutic preparation defined in DE-OS No. 32 20 326. Histological studies have shown that the combination according to the invention is effective to attack and destroy tumor cells, especially while they are quiescent, to a significantly higher degree than the previously described therapeutic preparation already mentioned, which preparation is only partially effective in successfully fighting quiescent tumor cells. In view of the fact set forth initially, i.e. that the cells of most types of cancer are preponderantly quiescent, this novel effect of the combination according to the invention is of utmost importance. Thus, it will permit the cells of presumably all types of cancer to be fought permanently, i.e. while they are dividing and when they are quiescent.

This enhanced efficacy of the substances combined in accordance with the invention will additionally cause a further increase in selectivity since hardly any or possibly no cytotoxically or cytolytically effective substances will be ineffective against quiescent tumor cells; thus, they are prevented from subsequently invading healthy cells. The side effects of cytostatic chemotherapy can therefore be further reduced, above all since dosage levels of cytostatic agents can be further reduced.

Another novel advantage of the combination according to the invention is the substantial reduction in antigenic reactions to high-molecular glycosaminoglycan poylsulfates due to the addition of low-molecular glycosaminoglycan polysulfates. However, it would not be appropriate to use nothing but low-molecular glycosaminoglycan polysulfates because their therapeutic anti-carcinoma efficacy is not comparable to the one characterizing higher-molecular glycosaminoglycan polysulfates.

The mixtures of glycosaminoglycan polysulfates according to the invention have been found to be characterized more particularly by having an increased efficacy whenever tumors have already attained high cell counts. Even though there is still no conclusive scientific explanation for this increase in selectivity, it is assumed that the special type and the degree of sulfation is responsible for the phenomenon observed.

In an advantageous embodiment of this invention, said high-molecular glycosaminoglycan polysulfates have molecular weights of between more than 5,000 and up to 15,000, preferably within the range from 8,000 to 12,000. The low-molecular glycosaminoglycan polysulfates used advantageously have a molecular weight within the range from 1,500 to 5,000, preferably within the range from 1,500 to 3,000.

As a low-molecular glycosaminoglycan polysulfate, pentosan polysulfate has been found to be particularly advantageous, more particularly as an alkali salt, and above all as a sodium salt.

Related to parts per weight of active substances, the weight ratio of glycosaminoglycan polysulfates to cytostatic agents ranges from 10:1 to 1:10.

Cytostatic drug quantities depend upon the type of cytostatic agent used.

For conversion into medicaments, the preparations are mixed, in a manner known per se, with suitable pharmaceutical carrier substances, aromatics, flavorings and colorants and configured, for instance, into tablets or dragées, or suspended or solved in water or oil, e.g. olive oil, upon addition of suitable auxiliary substances.

Preparations can be administered in liquid or solid form, or else parenterally. The injection medium used preferentially is water containing the stabilizers, solutes and/or buffers usual in injection solutions. Such additives include, for instance, tartrate or borate buffers, ethanol, dimethyl sulfoxide, complexing agents (such as ethylene diamine tetraacetic acid), high-molecular polymers (such as liquid polyethylene oxide) used to adjust viscosities, or polyethylene derivatives of sorbit anhydrides.

Solid carriers are, e.g., starch, lactose, mannite, methyl cellulose, talcum, highly dispersed silicic acid, higher-molecular fatty acids (such as stearic acid), gelatine, agar agar, calcium phosphate, magnesium stearate, animal or vegetable fats, or solid, high-molecular polymers (such as polyethylene glycols). Preparations suitable for oral administration may, if required, contain flavorings and sweeteners.

Therapeutically effective individual doses of the preparation range between 5 mgs and 500 mgs.

The invention will not be exemplified by the experiment described below, wherein the following pharmacologically active substances were used:

(a) glycosaminoglycan polysulfates:
  1. mucopolysaccharide polysulfate acid ester (MPS); molecular weight: 10,000
  2. sodium pentosan polysulfate (PSS); molecular weight: 2,000
(b) cytostatic drug: mitomycin
(c) enzyme: trypsin (pure preparation)

EXPERIMENT 60 rats (Wistar) of the same sex were randomized into three groups.

Every single animal received 10,000,000 cells of Yoshida-Ascites carcinoma (hemorrhagic). Individual groups were treated by means of the following active substances:

Group A: MPS+PSS+mitomycin
Group B: MPS+PSS+mitomycin+trypsin
Group C: controls

The active substances were administered to the rats at the following dosage levels per kg of live weight:

| | |
|---|---|
| MPS | 5 mg/kg of l.w. |
| PSS | 5 mg/kg of l.w. |
| Mitomycin | 0.4 mg/kg of l.w. |
| Trypsin | 0.2 mg/kg of l.w. |

Commencement of therapy: 48 hours upon transfer of tumor.

Group A animals received a total of 4 injections each at 48-hour intervals.

Group B animals received 3 injections each, likewise at intervals of 48 hours.

3 weeks upon the last injection, the experiment was evaluated. Results were as set forth in the table below:

TABLE

| Group of 20 animals | live | having no tumor | dead | having a tumor |
|---|---|---|---|---|
| A | 19 | 19 | 1 | 0 |
| B | 20 | 20 | 0 | 0 |
| C | 0 | 0 | 20 | 20 |

The experiment showed that, in group B, 3 injections obtained the same effect as 4 injections in group A. In view of the fact that there are different levels of resistance among the various types of tumors and cells, none of the effective combinations quoted herein can be dispensed with.

It has been shown that the cytostatic effect produced by MPS and PSS, both alone and in combination, is insufficient. The same is true of mitomycin and trypsin.

What is claimed is:

1. A therapeutic preparation comprising glycosaminoglycan polysulfates and at least one cytostatic agent in addition to a pharmaceutically acceptable carrier, characterized in that said glycosaminoglycan polysulfates are present as a mixture of high-molecular glycosaminoglycans having a molecular weight within the range from above 5,000 to 15,000 and low-molecular glycosaminoglycan polysulfates having a molecular weight within the range from 1,500 to 5,000 whereby said cytostatic agent is selected from the group consisting of alkylating cytostatic agents, antimetabolites, antagonists of purine and pyrimidine bases, cytostatically effective antibiotics and alkaloids.

2. A therapeutic preparation according to claim 1, characterized in that it contains at least one enzyme selected from the group of proteolytic and lipolytic enzymes.

3. A therapeutic preparation according to claim 1, characterized in that said high-molecular glycosaminoalycan polysulfate has a molecular weight within the range from above 8,000 to 12,000, and said low-molecular glycosaminoglycan polysulfate has a molecular weight within the range from 1,500 to 3,000.

4. A therapeutic preparation according to claim 1 or claim 2 or claim 3, characterized in that said low-molecular glycosaminoglycan polysulfate is a pentosan polysulfate.

5. A therapeutic preparation according to claim 2 or claim 3, characterized in that said additional enzyme is trypsin.

6. A therapeutic preparation according to claim 1 or claim 2 or claim 3, characterized in that the quantitative ratio between high-molecular and low-molecular glycosaminoglycan polysulfates to cytostatic agents ranges from 1:10 to 10:1.

7. A therapeutic preparation according to claim 4, characterized in that said additional enzyme is trypsin.

8. A therapeutic preparation according to claim 4, characterized in that the quantitative ratio between high-molecular and low-molecular glycosaminoglycan polysulfates to cytostatic agents ranges from 1:10 to 10:1.

9. A therapeutic preparation according to claim 6 characterized in that the quantitative ratio between high-molecular and low-molecular glycosaminoglycan polysulfates to cytostatic agents ranges from 1:10 to 10:1.

10. A therapeutic preparation according to claim 1 wherein said alkylating cytostatic agent is selected from the group consisting of nitrogenous mustard-gas and ethylene imine derivatives.

11. A therapeutic preparation according to claim 1 wherein said antimetabolite is methotrexate.

12. A therapeutic preparation according to claim 1 wherein said alkaloids are selected from a group consisting of cholchicine and vincristin.

13. A therapeutic preparation according to claim 2 characterized in that said pentosan polysulfate is sodium pentosan polysulfate.

* * * * *